(12) United States Patent
Schnaubelt et al.

(10) Patent No.: US 7,473,778 B2
(45) Date of Patent: Jan. 6, 2009

(54) 3-(4-PIPERIDINYL)-2,3,4,5-TETRAHYDRO-1,3-BENZODIAZEPIN-2(1H)-ONE

(75) Inventors: Juergen Schnaubelt, Oberhoefen/Warthausen (DE); Emanuel Stehle, Ravensburg (DE); Thomas Krueger, Kisslegg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 68 days.

(21) Appl. No.: 11/567,429

(22) Filed: Dec. 6, 2006

(65) Prior Publication Data

US 2008/0009617 A1   Jan. 10, 2008

(30) Foreign Application Priority Data

Dec. 24, 2005   (EP) .................. 05028476

(51) Int. Cl.
   *C07D 243/04*   (2006.01)
(52) U.S. Cl. .................................... 540/500
(58) Field of Classification Search ........... 540/500
   See application file for complete search history.

(56) References Cited

U.S. PATENT DOCUMENTS

| 3,474,090 | A | 10/1969 | Wright |
| 7,141,667 | B2 | 11/2006 | Schnaubelt et al. |
| 2004/0204397 | A1 | 10/2004 | Chaturvedula et al. |

FOREIGN PATENT DOCUMENTS

| CA | 2361939 A1 | 9/2000 |
| EP | 1619187 A1 | 1/2006 |
| WO | 0055154 A1 | 9/2000 |
| WO | 2005065779 A1 | 7/2005 |
| WO | 2006010511 A1 | 2/2006 |

OTHER PUBLICATIONS

Papot, et al; Study of Biscarbamates Derived from 2-Aminobenzylamines as Models for Alcohol Prodrugs; Tetrahedron 55; 1999; pp. 4699-4708.
Vaidya, et al; Synthesis of naphtho[2,1-b]furo[3,2-e]-1,4-diazepin-2-ones and naphtho[2,1-b]furo[3,2-e]-1,3,4-triazepin-2-ones of pharmacological interest; Indian Journal of Chemistry-B; vol. 43B; Jul. 2004; pp. 1537-1543.
International Search Report (Form PCT/ISA/220) for corresponding PCT/EP2006-070067.
Mayer, P. et al., New Substituted 1(2,3-Dihydrobenzol[1,4]dioxin-2-ylmethyl)piperidin-4yl Derivatives with alpha 2-Adrenoceptor Antagonist Activity, J. Med. Chem. 2000, 43, 3653-3664.

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to a process for preparing the compound 3-(4-piperidinyl)-2,3,4,5-tetrahydro-1,3-benzodiazepin-2(1H)-one of formula which is to be found as a structural element in CGRP antagonists which are suitable above all for the oral therapy of migraine.

(I)

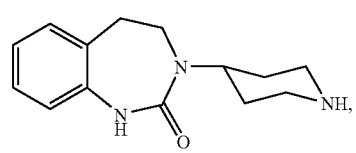

20 Claims, No Drawings

3-(4-PIPERIDINYL)-2,3,4,5-TETRAHYDRO-1,3-BENZODIAZEPIN-2(1H)-ONE

The present invention relates to a process for preparing the compound 3-(4-piperidinyl)-2,3,4,5-tetrahydro-1,3-benzodiazepin-2(1H)-one of formula I

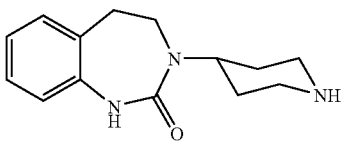

which is to be found as a structural element in CGRP antagonists which are suitable above all for the oral therapy of migraine.

BACKGROUND TO THE INVENTION

Examples of compounds with CGRP-antagonistic properties which contain as structural element the compound of formula I are described in International Patent Applications PCT/EP97/04862, PCT/EP00/02004, PCT/EP00/13236, PCT/EP03/02417, PCT/EP03/11762 and PCT/EP03/11763.

BRIEF SUMMARY OF THE INVENTION

The present application relates to a process for preparing the compound 3-(4-piperidinyl)-2,3,4,5-tetrahydro-1,3-benzodiazepin-2(1H)-one of formula I. The process according to the invention leads in a few steps to good yields of the desired compound, which is also obtained in a very pure form.

DETAILED DESCRIPTION OF THE INVENTION

2-Nitrophenylacetic acid may be used as starting material for the compound of formula I. In a first step it is reacted with an equimolar solution of 4-amino-N-phenylmethylpiperidine in the presence of at least one equivalent, preferably 1.1 to 1.5 equivalents, particularly preferably 1.1 equivalents, of condensing agent such as carbonyldiimidazole, carbonylditriazole, n-propanephosphonic anhydride, dicyclohexylcarbodiimide, thionyl chloride, TBTU O-(benzotriazol-1-yl)-N,N,N',N'-tetramethyluronium tetrafluoroborate or 1-ethyl-3-(3'-dimethylaminopropyl)-carbodiimide to form the 2-nitro-N-[1-(phenylmethyl)-4-piperidinyl]-phenylacetamide of formula II

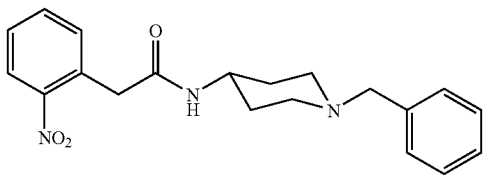

Suitable solvents are polar aprotic solvents such as tetrahydrofuran, 2-methyltetrahydrofuran, dimethoxyethane, toluene, dimethylformamide or N-methylpyrrolidinone. The product may e.g. be crystallised by diluting with water and worked up by filtration or centrifugation and drying.

In the following step the 2-nitro-N-[1-(phenylmethyl)-4-piperidinyl]-phenylacetamide of formula II is first dissolved in a polar organic solvent, such as for example methanol, ethanol, isopropanol, dimethylformamide, N-methylpyrrolidinone, 2-methyltetrahydrofuran, tetrahydrofuran, dioxane or dimethoxyethane, and the nitro group hydrogenated by the addition of a metal catalyst, preferably 2.5 to 20%, particularly preferably 4 to 6%, to form a compound of formula III

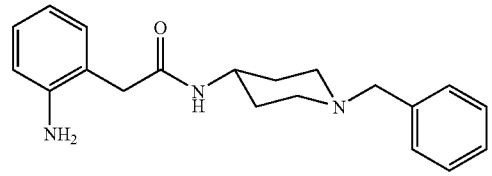

Catalysts which may be used are Raney nickel or platinum dioxide. Advantageous conditions for the hydrogenation are temperatures of 20 to 60° C. and an excess hydrogen pressure of not more than 3 bar. After the catalyst has been filtered off the hydrogenation product may be concentrated by distilling off the solvent.

Then the crude product of formula II is carbamoylated in solution by the addition of at least one equivalent, preferably 1.0 to 2.0 equivalents, particularly preferably 1.6 equivalents, an ester and in the presence of at least one equivalent, preferably 1.0 to 2.0 equivalents, particularly preferably 1.6 equivalents, of a base to obtain a carbamate of general formula IV

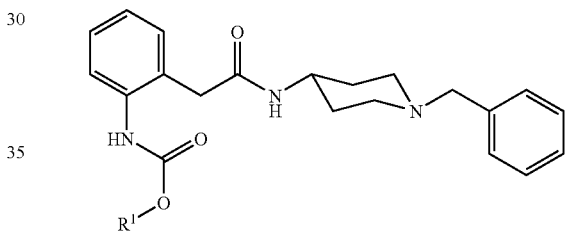

wherein $R^1$ denotes a phenyl, benzyl, an allyl, 2,2,2-trichloroethyl, or a straight-chain or branched $C_{1-6}$-alkyl group, for example the methyl, ethyl, propyl, iso-propyl, butyl, iso-butyl, tert.-butyl, pentyl, neopentyl or hexyl group.

Esters which may be used are di-tert.butyl pyrocarbonate or a chloroformic acid ester, for example allyl, methyl, ethyl, 2,2,2-trichloroethyl, propyl, iso-propyl, butyl, isobutyl, pentyl, neopentyl, hexyl, phenyl or benzyl chloroformate. The base used may be either an aliphatic amine, such as for example N-methylmorpholine, or an aqueous solution of sodium carbonate, potassium carbonate, sodium hydroxide, ammonia or potassium hydroxide. Water is added to the reaction mixture and after phase separation the organic phase is concentrated in vacuo.

The product may for example be crystallised out by the addition of an acetone-water mixture. The product may then be worked up by filtration or centrifugation and drying.

In the following key step the compound of general formula IV is first dissolved in an aprotic organic solvent, such as for example toluene, 2-methyltetrahydrofuran, tetrahydrofuran or dimethoxyethane and the carbonyl group is converted into a methylene group by the addition of at least 2 equivalents, preferably 4.0 to 8.0 equivalents, of a reducing agent. The reducing agent used may be for example borane, diisobutylaluminium hydride, lithium aluminium hydride, lithium or sodium borohydride, optionally with the addition of at least 0.5 equivalents, preferably 2.0 to 4.0 equivalents, of a Lewis acid, an acid or a halogen, for example with the addition of sulphuric acid, chlorotrimethylsilane or iodine. The reduction may be carried out at temperatures of 20 to 100° C., preferably at 60 to 80° C. Under these conditions cyclisation is carried out to form 3-[1-(phenylmethyl)-4-piperidinyl]-2,3,4,5-tetrahydro-1,3-benzodiazepin-2(1H)-one of formula V

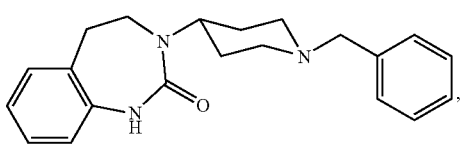

which after aqueous working up can be precipitated by diluting with alcohol, for example methanol, ethanol or isopropanol, preferably methanol, and worked up by filtration or centrifugation and drying.

In the last step the benzyl protecting group of the 3-[1-(phenylmethyl)-4-piperidinyl]-2,3,4,5-tetrahydro-1,3-benzodiazepin-2(1H)-one of formula V is cleaved. To do this the starting material is dissolved in a polar solvent, such as for example methanol, ethanol, water, acetone, tetrahydrofuran, dimethylformamide or propanol, and hydrogenated in a pressurised reactor. The hydrogenating agent used may be for example Pd/C or Pd(OH)$_2$. Advantageous conditions for the hydrogenation are temperatures of 40 to 80° C. and an excess hydrogen pressure of not more than 3 bar. After the catalyst has been filtered off the hydrogenation product 3-(4-piperidinyl)-2,3,4,5-tetrahydro-1,3-benzodiazepin-2(1H)-one of formula I may be crystallised by concentrating the solvent and subsequently adding acetone or water, then filtered off and dried.

EXPERIMENTAL SECTION

EXAMPLE 1

2-Nitro-N-[1-(phenylmethyl)-4-piperidinyl]-phenylacetamide

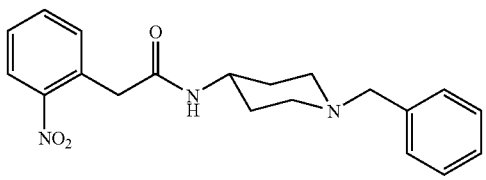

11.81 kg (72.87 mol, 1.1 eq) 1,1-carbonyldiimidazole (CDI) are provided at 20° C. and 18 L tetrahydrofuran are added. Then 12.00 kg (66.24 mol, 1.0 eq) 2-nitrophenylacetic acid, dissolved in 24 L tetrahydrofuran, are added within 15 minutes. The feed vessel is rinsed with 9 L tetrahydrofuran and the reaction mixture is stirred for 30 minutes (gas given off: $CO_2$). Then a vacuum of 300 mbar is applied twice in order to eliminate excess $CO_2$.

12.61 kg (66.24 mol, 1.0 eq) 4-amino-N-phenylmethylpiperidine in 6 L tetrahydrofuran are added to the solution at 20° C. (exothermic). After the addition the reaction mixture is stirred for a further 2 hours at 20° C. Then 144 L water are added; after the addition of ¼ of the amount of water the solution is inoculated with 2-nitro-N-[1-(phenylmethyl)-4-piperidinyl]-phenylacetamide. The suspension obtained is cooled to 0 to 5° C. and stirred for a further hour to complete the crystallisation. Then the product is removed by centrifuging, washed with a cold mixture of 160 L water and 9 L tetrahydrofuran and dried in the drying cupboard at 45° C. while being rendered inert.

Yield: 18.21 kg (77.8% of theory) Chemical purity according to HPLC: 99.8%

EXAMPLE 2

2-Amino-N-[1-(phenylmethyl)-4-piperidinyl]-phenylacetamide

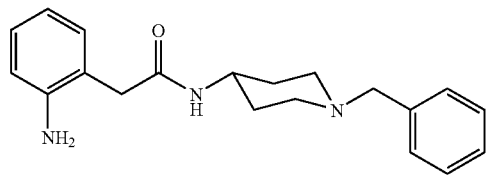

20.00 g (56.59 mmol, 1.0 eq) 2-nitro-N-[1-(phenylmethyl)-4-piperidinyl]-phenylacetamide from Example 1 are placed in 280 mL 2-methyltetrahydrofuran. The solution is hydrogenated in the presence of 2.00 g platinum dioxide at 20° C. The catalyst is filtered off and washed with 20 ml of 2-methyltetrahydrofuran. The product is not isolated, but used as a solution in the next step.

EXAMPLE 3

2-Methoxycarbonylamino-N-[1-(phenylmethyl)-4-piperidinyl]-phenylacetamide

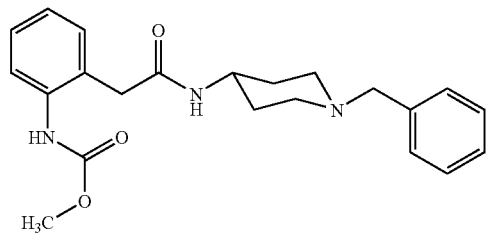

50 ml of 2-methyltetrahydrofuran are distilled off from the solution consisting of 9.15 g (28.29 mmol, 1.0 eq) 2-amino-N-[1-(phenylmethyl)-4-piperidinyl]-phenylacetamide in 162 ml of 2-methyltetrahydrofuran. The solution is cooled to −12° C. and 4.56 g (45.10 mmol, 1.6 eq) 4-methylmorpholine are added, followed by 4.26 g (45.10 mmol, 1.6 eq) methyl chloroformate. The reaction mixture is stirred for another 1 hour at 20° C. and then combined with 100 ml of water. After phase separation the aqueous phase is washed with 20 ml 2-methyltetrahydrofuran and the combined organic phases are washed with 50 ml of water. The organic solvent is distilled off in vacuo. The residue is combined with 50 ml of acetone and refluxed. Then 100 ml of water are added and the suspension obtained is cooled to 20° C. To complete the crystallisation the mixture is stirred for 30 minutes at 20° C. Then the product is suction filtered, washed with 30 ml acetone-water mixture (1:2) and dried in the dryer at 45° C. while being rendered inert.

Yield: 8.68 g (80.0% of theory) Chemical purity according to HPLC: 96.8%

EXAMPLE 4

3-[1-(Phenylmethyl)-4-piperidinyl]-2,3,4,5-tetrahydro-1,3-benzodiazepin-2(1H)-one

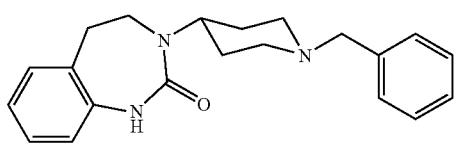

5.00 g (13.11 mmol, 1.0 eq) 2-methoxycarbonylamino-N-[1-(phenylmethyl)-4-piperidinyl]-phenylacetamide from Example 3 are suspended in 50 ml of toluene and heated to 80° C. At this temperature 56.1 g (78.61 mmol, 6.0 eq) diisobutylaluminium hydride in toluene (20%) are metered in. After the addition has ended the reaction mixture is stirred for another 30 minutes at this temperature. After cooling to 10° C. the mixture is adjusted to pH=2.5 with hydrochloric acid. The precipitate formed is dissolved with sodium hydroxide solution and after phase separation the organic phase is washed with 50 ml of water. The organic phase is evaporated down in vacuo to an oil and combined with 50 ml of methanol.

The solution obtained is refluxed and slowly cooled to −15° C. Then the precipitate is filtered off and dried at 50° C. in the drying cupboard.

Yield: 1.86 g (42% of theory)

EXAMPLE 5

3-(4-Piperidinyl)-2,3,4,5-tetrahydro-1,3-benzodiazepin-2(1H)-one

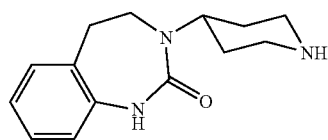

10.00 kg (29.81 mol, 1.0 eq) 3-[1-(phenylmethyl)-4-piperidinyl]-2,3,4,5-tetrahydro-1,3-benzodiazepin-2(1H)-one from Example 3 are dissolved in 100 L methanol, combined with 1.00 kg 10% Pd/C and hydrogenated in the pressurised reactor at 70° C. and 3 bar. After the hydrogen uptake has ended the catalyst is filtered off and washed with 30 L methanol. The filtrate is concentrated in vacuo and the residue is suspended in 100 L acetone. Then the mixture is refluxed, the suspension is stirred for 15 minutes at reflux temperature and half the acetone is distilled off at normal pressure. After the distillation has ended the mixture is cooled to 0° C. and stirred for a further hour. The product is suction filtered, washed with 20 L acetone and dried at 50° C.

Yield: 6.17 kg (84.3% of theory) Chemical purity according to HPLC: 99.8%

The invention claimed is:

1. A process for preparing the compound of formula I

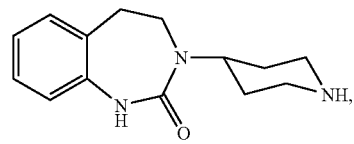

wherein (a) 2-nitrophenylacetic acid is reacted with 4-amino-N-phenylmethylpiperidine to form 2-nitro-N-[1-(phenylmethyl)-4-piperidinyl]-phenylacetamide of formula II

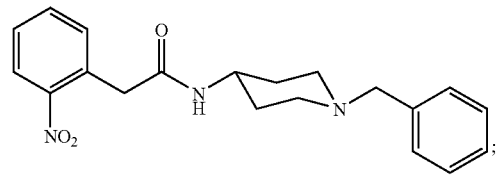

(b) the nitro group of the 2-nitro-N-[1-(phenylmethyl)-4-piperidinyl]-phenylacetamide of formula II obtained is hydrogenated to form the amino group, thereby producing the compound of formula III

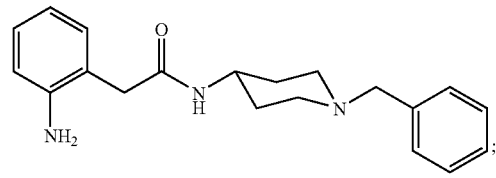

(c) the intermediate product of formula III obtained is reacted by the addition of an ester and in the presence of a base to form a carbamate of general formula IV

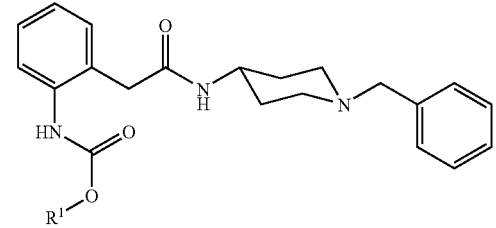

wherein $R^1$ denotes a phenyl, benzyl, allyl, 2,2,2-trichloroethyl or a straight-chain or branched $C_{1-6}$-alkyl group, and (d) the compound of general formula IV obtained is dissolved in an aprotic organic solvent, the carbonyl group is converted into a methylene group by the addition of a reducing agent and cyclised to form 3-[1-(phenylmethyl)-4-piperidinyl]-2,3,4,5-tetrahydro-1,3-benzodiazepin-2(1H)-one of formula V

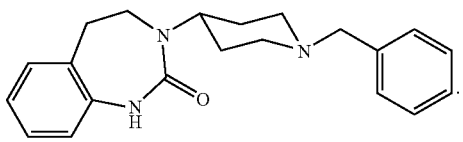

2. The process according to claim 1, wherein, in step (a), the 4-amino-N-phenylmethylpiperidine is added as a solution in a polar aprotic solvent and the reaction is carried out in the presence of a condensing agent.

3. The process according to claim 2, wherein tetrahydrofuran, 2-methyltetrahydrofuran, dimethoxyethane, toluene, dimethylformamide or N-methylpyrrolidinone is used as the polar aprotic solvent.

4. The process according to claim 2, wherein, in step (a), carbonyldiimidazole, carbonylditriazole, n-propanephosphonic anhydride, dicyclohexylcarbodiimide, thionyl chloride, TBTU O-(benzotriazol-1-yl)-N,N,N',N'-tetramethyluronium tetrafluoroborate or 1-ethyl-3-(3'-dimethylaminopropyl)-carbodiimide are used as condensing agents.

5. The process according to claim 2, wherein, in step (a), 1.1 to 1.5 equivalents of the condensing agent are added.

6. The process according to claim 1, wherein the product obtained in step (a) is crystallised out by diluting with water.

7. The process according to claim 1, wherein the reaction in step (b) is carried out in a polar organic solvent and by the addition of a catalyst.

8. The process according to claim 7, wherein, in step (b), methanol, ethanol, isopropanol, dimethylformamide, N-methylpyrrolidinone, 2-methyltetrahydrofuran, tetrahydrofuran, dioxane or dimethoxyethane is used as the polar organic solvent.

9. The process according to claim 7, wherein, in step (b), Raney nickel or platinum dioxide is used as catalyst and the hydrogenation is carried out at a temperature of 20 to 60° C. and under an excess hydrogen pressure of not more than 3 bar.

10. The process according to claim 7, wherein the catalyst in step (b) is added in an amount of 2.5 to 20%.

11. The process according to claim 1, wherein, in step (c), 1.0 to 2.0 equivalents of an ester are added.

12. The process according to claim 1, wherein, in step (c), di-tert.butyl pyrocarbonate or a chloroformic acid ester is used as the ester.

13. The process according to claim 1, wherein, in step (c), 1.0 to 2.0 equivalents of the base are added.

14. The process according to claim 1, wherein, in step (c), N-methylmorpholine or an aqueous solution of sodium carbonate, potassium carbonate, sodium hydroxide, ammonia or potassium hydroxide is used as base.

15. The process according to claim 1, wherein the starting material in step (d) is dissolved in an aprotic organic solvent and after the addition of a hydrogenating agent the mixture is hydrogenated in a pressurised reactor at temperatures of 40 to 80° C. and under an excess hydrogen pressure of not more than 3 bar.

16. The process according to claim 11, wherein toluene, 2-methyltetrahydrofuran, tetrahydrofuran or dimethoxyethane is used as the aprotic organic solvent.

17. The process according to claim 1, wherein, in step (d), the reducing agent is added in an amount of at least 2 equivalents.

18. The process according to claim 1, wherein, in step (d), borane, diisobutylaluminium hydride, lithium or sodium borohydride is used as reducing agent.

19. The process according to claim 1, wherein the product 3-[1-(phenylmethyl)-4-piperidinyl]-2,3,4,5-tetrahydro-1,3-benzodiazepin-2(1H)-one obtained in step (d) is precipitated by diluting with water and alcohol.

20. The process according to claim 1, wherein 3-[1-(phenylmethyl)-4-piperidinyl]-2,3,4,5-tetrahydro-1,3-benzodiazepin-2(1H)-one of formula V obtained in step (d) is converted into the compound of formula I by cleaving the benzyl protecting group.

* * * * *